US011285181B2

(12) United States Patent
Roos

(10) Patent No.: US 11,285,181 B2
(45) Date of Patent: Mar. 29, 2022

(54) LACTIC ACID BACTERIA, METHODS AND USES THEREOF

(71) Applicant: BIOGAIA AB, Stockholm (SE)

(72) Inventor: Stefan Roos, Uppsala (SE)

(73) Assignee: Biogaia AB, Stockholm (SE)

( * ) Notice: Subject to any disclaimer, the term of this patent is extended or adjusted under 35 U.S.C. 154(b) by 83 days.

(21) Appl. No.: 16/496,509

(22) PCT Filed: Mar. 27, 2018

(86) PCT No.: PCT/EP2018/057765
§ 371 (c)(1),
(2) Date: Sep. 23, 2019

(87) PCT Pub. No.: WO2018/178072
PCT Pub. Date: Oct. 4, 2018

(65) Prior Publication Data
US 2020/0038461 A1    Feb. 6, 2020

(30) Foreign Application Priority Data
Mar. 27, 2017 (SE) .................................. 1750363-2

(51) Int. Cl.
A61K 35/747 (2015.01)
C12N 1/20 (2006.01)
A61K 35/00 (2006.01)
C12R 1/225 (2006.01)

(52) U.S. Cl.
CPC ............ *A61K 35/747* (2013.01); *C12N 1/205* (2021.05); *A61K 2035/115* (2013.01); *C12R 2001/225* (2021.05)

(58) Field of Classification Search
None
See application file for complete search history.

(56) References Cited

FOREIGN PATENT DOCUMENTS

| JP | 09163976 | 6/1997 | | |
|---|---|---|---|---|
| JP | 2005304362 A | 11/2005 | | |
| JP | 2012180289 A | 9/2012 | | |
| WO | WO-2010124855 A1 * | 11/2010 | ........... | A61K 35/744 |
| WO | 2018/083336 | 5/2018 | | |

OTHER PUBLICATIONS

Karimi et al. Physiol Rep, 6(2), 2018 e13514, https://doi.org/10.14814/phy2.13514.*
Written Opinion and International Search Report corresponding to International Patent Application No. PCT/EP2018/057785, dated Jul. 11, 2018, 10 pages.
Bertin et al. "Enterohaemorrhagic *Eschericia coli* gains a competitive advantage by using ethanolamine as a nitrogen source in the bovine intestinal content: EHEC uses ethanolamine as a nitrogen source in the bovine intestine" Environmental Microbiology, 13(2):365-377 (2010).
De Angelis et al. "Lactobacillus rossiae, a Vitamin 812 Producer, Represents a Metabolically Versatile Species within the Genus *Lactobacillus*" PLOS ONE. 9(9):1-11 (2014).
Kamada et al. "Control of pathogens and pathobionts by the gut microbiota" Nature Immunology; 14(7):685-690 (2013).
Kaval et al. "Ethanolamine Utilzation in Bacteria"; mBio, 9(1):1-13, URL: http://mbio.asm.org/content/9/1/e00066-18.full.pdf#page=1&view=FitH (2018).
Moal et al. "Ant-Infective Activities of *Lactobacillus* Strains in the Human Intestinal Miorobiota: from Probiotics to Gastrointestinal Anti-Infectious Biotherapeutic Agents" Clinical Microbiology Reviews. 27(2):187-199 (2014).
Thiennimitr et al. "Intestinal inflammation allows *Salmonella* to use ethanolamine to compete with the microbiota" Proceedings of the National Academy of Sciences, 108(42):17480-17485 (2011).
Archambaud et al. "Impact of lactobacilli on orally acquired listeriosis" PNAS, 109(41):16684-16689 2012.

* cited by examiner

*Primary Examiner* — Oluwatosin A Ogunbiyi
(74) *Attorney, Agent, or Firm* — Myers Bigel, P.A.

(57) ABSTRACT

The present invention relates to novel strains of lactic acid bacteria, more specifically, novel strains of *Lactobacillus reuteri*, capable of utilizing ethanolamine. This characteristic makes it possible for the bacteria to compete for the same substrate as pathogenic ethanolamine-utilizing pathogens, thereby presenting an effective means to combat infections resulting from such pathogenic bacteria. There is also provided a method of selecting further ethanolamine-utilizing lactic acid bacteria, as well as other methods and uses involving said novel strains and other ethanolamine-utilizing lactic acid bacteria.

7 Claims, 3 Drawing Sheets

LACTIC ACID BACTERIA, METHODS AND USES THEREOF

STATEMENT OF PRIORITY

This application is a 35 U.S.C. § 371 national phase application of International Application Serial No. PCT/EP2018/057765, filed Mar. 27, 2018, which claims the benefit, of Swedish Patent Application No. 1750363-2, filed Mar. 27, 2017, the entire contents of each of which are incorporated by reference herein.

TECHNICAL FIELD OF THE INVENTION

The present invention concerns lactic acid bacteria and particularly lactic acid bacteria with beneficial effects on disorders or conditions in humans and animals and to the use of said lactic acid bacteria as probiotics. More particularly, the invention concerns the activation of certain biological activities in lactic acid bacteria which are beneficial to the health of human beings upon administration of the lactic acid bacteria to said human beings.

BACKGROUND OF THE INVENTION

It is well established that interactions between host and microbe are fundamental to health and disease. The microbiota generates metabolites that provide the host with nutrients and are further involved in the immune response and regulation and development of the immune system. The tissue microenvironment determines the composition of the microbiota, which in turns means that one way to influence and change the microbiota composition might be through alterations of the diet (such as sugar, fat or fiber—which function as energy sources for bacteria). Alterations in host immunity, either as a result of genetic variation or concurrent infections and consequent use of antibiotics, can also influence the microbiota in the gut.

*Lactobacillus* and other lactic acid producing bacteria such as bifidobacteria are commonly used as probiotics in various types of foods, for example yoghurt. Growth and colonization of harmful microorganisms can be prevented by lactic acid producing bacteria through their own colonization on or inside the mammal, through formation of biofilms, through competition of available nutrients and also the production of specific substances such as hydrogen peroxides, bacteriocins, or organic acids (including lactic acid and acetic acid) that lower the pH.

*Lactobacillus reuteri* is a bacterium known to produce the antimicrobial substance 3-hydroxypropionaldehyde (HPA), also called reuterin.

Cells of prokaryotes have been viewed as primitive, although some contain unusual enclosures known as microcompartments (MCS), which appear to serve as primitive organelles inside bacterial cells. The carboxysome (which is involved in fixing carbon dioxide) was for nearly 30 years the only microcompartment recognized within microbial cells. In 2005, professor Todd O. Yeates and his colleagues revealed the first structural details of bacterial microcompartments. The first high-resolution structures of the bacterial microcompartment proteins reveal principles of construction highly similar to those seen in some viruses. Six identical protein subunits come together to form a hexameric unit, which constitutes the building block for the shell. These hexameric units pack tightly together to form a molecular layer that contains only tiny pores. This tight packing appears to restrict movement of molecules into and out of the microcompartment, except through the pores.

Cluster analysis of homologues of microbial microcompartment-specific proteins suggests that such enclosures could be involved in as many as seven different metabolic processes in various bacterial species (Thomas A. Bobik. 2007. Bacterial Microcompartments. Microbe. 1:25-31.). The building blocks of bacterial microcompartments are exclusively proteins and glycoproteins. Electron microscopy (required to observe microcompartments) shows no lipid monolayer or bilayer (as in vesicles of the eukaryotes) surrounding such microcompartments, making them the only known protein-based metabolic compartments in living cells.

Members of bacterial genera, including *Salmonella, Escherichia, Klebsiella, Clostridium, Fusobacterium, Shigella, Listeria,* and *Yersinia,* contain the components needed for degrading ethanolamine in their microcompartments. Another property of microcompartments is thought to be their ability to act as containers for substrates toxic for the bacteria itself.

Ethanolamine is a breakdown product of the membrane phospholipid phosphatidylethanolamine (PE) and is prevalent in the gastrointestinal tract. Ethanolamine can be used as a source of nitrogen (and sometimes carbon) by bacteria capable of catabolizing this compound. This capability has been associated with important gastrointestinal pathogens, including for example enterohemorrhagic *Escherichia coli* O157:H7 (EHEC) Ethanolamine might also be a signal for the bacteria to initiate its virulence program. (Garsin D A. 2012. Ethanolamine: a signal to commence a host-associated lifestyle? mBio 3(4):e00172-12. doi:10.1128/mBio.00172-12.)

Rising antimicrobial resistance and dwindling new antibiotic discovery are increasing the risk of a global infectious disease healthcare crisis. The National Action Plan to Combat Antibiotic-Resistant Bacteria (Bacteria TFfCA-R (ed). 2015. *National Action Plan for Combating Antibiotic-Resistant Bacteria.* The White House, Washington, D.C.) emphasizes that efforts are needed to advance the development of new antibiotics and alternative therapies to fight resistance and diseases associated with antimicrobial use. As a result, a number of emerging therapies are being investigated, including but not limited to probiotics, immunotherapies, and toxin binding agents.

It is not an easy task to find a new antibiotic therapy since most pathogenic bacteria have developed clever ways to stay persistent and to take advantage of the host microenvironment in different situations. For example the pathogenic bacteria *Salmonella typhimurium* shows a unique growth advantage over other bacteria since they can utilize ethanolamine, which is a substance that is released by the host tissue cells in the inflamed gut. However, up until now, it was not believed, or at least not shown, that ethanolamine could be utilized by beneficial bacteria. See e.g. (Thiennimitr P, et. al *Intestinal inflammation allows Salmonella to use ethanolamine to compete with the microbiota,* Proc Natl Acad Sci USA 2011).

Hence, there is still a need in the art to identify new ways of combating pathogenic bacteria, and particularly a need for identifying new therapies that does not contribute to the further development of antibiotic resistance in the society.

SUMMARY OF THE INVENTION

The above objectives have now been solved or at least mitigated by the provision herein of novel strains of lactic acid bacteria capable of utilizing ethanolamine, methods to select further ethanolamine-utilizing lactic acid bacteria, methods for producing ethanolamine-utilizing lactic acid bacteria induced to utilize ethanolamine, as well as various compositions and uses involving said ethanolamine-utilizing lactic acid bacteria.

Accordingly, the present invention resides in the surprisingly finding that some lactic acid bacteria are able to utilize ethanolamine as a substrate. Without wishing to be bound by theory, this finding appears to provide a means for such bacteria to compete with pathogenic bacteria utilizing the same substrate. Hence, when such pathogenic bacteria are present in the gastrointestinal tract of an infected individual, where the substrate is available, administering beneficial ethanolamine-utilizing bacteria can render it possible for the bacteria to aggravate the pathogenic bacteria's survival and also decrease their virulence effect. It is also envisaged that other mechanisms already used by the ethanolamine-utilizing bacteria may interact with the ethanolamine-utilization mechanism and thereby provide an improved antimicrobial effect as presented herein. Accordingly, this presents a useful anti-microbial alternative targeting ethanolamine-utilizing pathogenic bacteria residing in the gastrointestinal tract of an individual. Subsequently, it is also envisaged that this finding has a potential to reduce excessive use of antibiotics in response to pathogenic infections. In addition, acetaldehyde produced by lactic acid bacteria when utilizing ethanolamine may have an antimicrobial effect of its own.

Hence, there is provided herein a method of selecting a lactic acid bacterial strain capable of utilizing ethanolamine, said method comprising the steps of:
  i) providing bacteria of a lactic acid bacterial strain in a culture medium and growing a culture of said bacteria,
  ii) determining if said bacteria are capable of utilizing ethanolamine; and
  iii) selecting said lactic acid bacterial strain if said bacteria are capable of utilizing ethanolamine,
  wherein said culture medium comprises an amount or concentration of ethanolamine and/or an amount or concentration of ethanolamine is added to the culture of step i) at a point in time before step ii).

In another aspect, there is also provided a method of selecting a lactic acid bacterial strain capable of utilizing ethanolamine comprising determining a genetic profile of said lactic acid bacteria, said method comprising the steps of:
  i) providing bacteria of a lactic acid bacterial strain to be screened;
  ii) performing an initial screening of said lactic acid bacterial strain, to determine the presence of one or more of the bacterial homologues of the genes encoding the following proteins;
    1. Ethanolamine ammonia lyase large subunit EutB;
    2. Microcompartment structural protein EutL; and/or
    3. Ethanolamine utilization protein EutH; in said lactic acid bacterial strain,
  iii) if one or more of said genes are present in said lactic acid bacterial strain, determining if said bacteria are capable of utilizing ethanolamine; and
  iv) selecting said lactic acid bacterial strain if said bacteria are capable of utilizing ethanolamine.

Optionally, a second or further screening, i.e. genetic screening, of said lactic acid bacterial strain may be performed, as a part of step ii), before or after step ii) and before step iii), or the like, of the above mentioned method, to determine the presence of one or more of the bacterial homologues of the genes encoding the following proteins:
  1. NADPH-dependent FMN reductase belonging to the pfam03358 protein family and/or
  2. Protein-tyrosine-phosphatase belonging to the pfam13350 protein family. Said genes of said second screening may be present in the same gene cluster or even in the same operon as the above mentioned genes screened in the initial screening. Preferably, said genes are present in the same gene cluster or even in the same operon.

Furthermore, there is also provided a method of producing lactic acid bacteria induced to utilize ethanolamine, said method comprising the steps of:
  i) providing lactic acid bacteria capable of utilizing ethanolamine in a culture medium,
  ii) adding to the culture medium of step i) a first amount or concentration of ethanolamine at a first point in time and growing said culture,
  iii) optionally adding to the culture of step ii) a second amount or concentration of ethanolamine at a second point in time and growing said culture, and thereafter;
  iv) retrieving the lactic acid bacteria from said culture medium.

Lactic acid bacteria selected or produced by a method disclosed herein are also encompassed by the present disclosure, as well as various uses thereof. In another aspect, there is also provided a composition comprising ethanolamine-utilizing lactic acid bacteria induced by ethanolamine during growing of a culture comprising said lactic acid bacteria.

As previously mentioned, there is also provided novel strains of *Lactobacillus reuteri:* a biologically pure culture of *Lactobacillus reuteri* DSM 27131 and a biologically pure culture of *Lactobacillus reuteri* DSM 32465. These strains have been selected as lactic acid bacterial strains that are capable of utilizing ethanolamine. These strains may also be used in a method for producing lactic acid bacteria induced to utilize ethanolamine, and in various other uses and methods encompassing ethanolamine-utilizing bacteria described herein. Also provided are frozen or lyophilized compositions of ethanolamine-utilizing lactic acid bacteria, such as *Lactobacillus reuteri,* e.g. a frozen or lyophilized composition comprising a biologically pure culture of *Lactobacillus reuteri* DSM 27131 and/or a biologically pure culture of *Lactobacillus reuteri* DSM 32465, said composition further comprising at least a cryoprotectant or a lyoprotectant. Different cryoprotectants (e.g. glycerol, sucrose, lactose or trehalose) or lyoprotectants (e.g. sucrose, lactose, trehalose or maltodextrin) as known in the art or other additives are also envisaged in the present context.

There is furthermore provided the novel strains, lactic acid bacteria selected by, or produced by, the methods disclosed herein, or as elsewhere described herein, for use as medicaments, such as for use in the treatment of a condition or disorder caused by or related to an ethanolamine-utilizing pathogen. Examples of such pathogens are further disclosed herein. There is also provided the use of said lactic acid bacteria or strains in inhibiting the growth of the one or more pathogenic bacteria. More specifically, these compositions are intended to be administered to humans or animals, for example for the purpose of a more efficient treatment of disorders induced by pathogens in the gastrointestinal tract.

DETAILED DESCRIPTION OF THE INVENTION

Definitions

Figure 1:
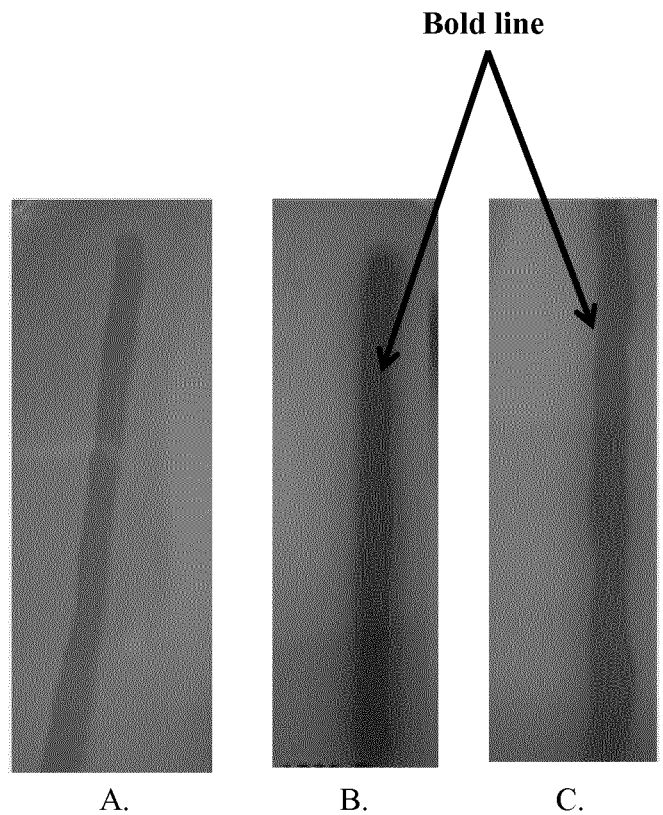
FIG. 1 shows the production of acetaldehyde by ethanolamine-utilizing lactic acid bacteria. The production of acetaldehyde is visualized as a (red) bold line accompanied by enlarged (red) zones surrounding said bold line. The bold line also comprises the bacterial streak; A) No bold line or red (i.e. enlarged) zones are seen around a bacterial streak of *L. reuteri* DSM 17938. B) Red (i.e. enlarged) zones extending approximately 3 mm on each side of the bacterial streak forming part of the bold line are seen around colonies of *L. reuteri* DSM 27131 and also red (enlarged) zones around a streak of *L. reuteri* DSM 32465 (C, extending approximately 1.5 mm on each side of the bacterial streak, said bacterial streak forming part of the bold line).

Herein, the term "treatment" may encompass both the alleviation of symptoms as well as preventing the onset of symptoms. Accordingly, this term includes prevention, reduction and prophylaxis of a condition or a disorder, or the like. The term "disorder" may also include a disease.

Whenever the term "bacteria" is used herein, this is intended to include lactic acid bacteria strains (unless a pathogen is intended), but is not limited to any particular strain.

The term "utilizing" ethanolamine is intended to refer to herein that lactic acid bacteria are capable of using and metabolizing ethanolamine into further active metabolites, according to a process known in the art. The term "utilizing" ethanolamine may in some contexts also refer to that lactic acid bacteria are capable of using and metabolizing ethanolamine into further active and secreted metabolites, according to other processes known in the art.

Lactic Acid Bacterial Strains

*Lactobacillus reuteri* strain DSM 27131 was deposited under the Budapest Treaty at the Leibniz-Institut DSMZ-Deutsche Sammlung von Mikroorganismen und Zellkulturen GmbH (Inhoffenstrasse 7B, D-38124 Braunschweig) on Apr. 18, 2013.

*Lactobacillus reuteri* strain DSM 32465 was deposited under the Budapest Treaty at the Leibniz-Institut DSMZ-Deutsche Sammlung von Mikroorganismen und Zellkulturen GmbH (Inhoffenstrasse 7B, D-38124 Braunschweig) on Mar. 21, 2017.

DEPOSIT INFORMATION

A deposit of the proprietary bacterial strain *Lactobacillus reuteri* DSM 27131 has been made with the Leibniz Institute DSMZ (DSMZ)—German Collection of Microorganisms and Cell Cultures, Inhoffenstr. 7B, D-38124 Braunschweig, Germany. The date of deposit for *Lactobacillus reuteri* DSM 27131 was Apr. 18, 2013. In addition, a deposit of the proprietary bacterial strain *Lactobacillus reuteri* DSM 32465 has been made with the Leibniz Institute DSMZ (DSMZ)—German Collection of Microorganisms and Cell Cultures, Inhoffenstr. 7B, D-38124 Braunschweig, Germany. The date of deposit for *Lactobacillus reuteri* DSM 27131 was Mar. 21, 2017. Upon issuance of a patent, all restrictions upon the deposits will be removed, and the deposits are intended to meet all of the requirements of 37 C.F.R. § 1.801-1.809. The DSMZ has issued accession number DSM 27131 for *Lactobacillus reuteri* DSM 27131 and accession number DSM 32465 for *Lactobacillus reuteri* DSM 32465. These deposits will be maintained in the depository for a period of 30 years, or 5 years after the last request, or for the effective life of the patent, whichever is longer, and will be replaced as necessary during that period. Applicants do not waive any infringement of their rights granted under this patent.

INTRODUCTION TO THE DETAILED DESCRIPTION

As previously mentioned herein the present inventors have for the first time identified novel non-pathogenic lactic acid bacterial strains that are capable of utilizing ethanolamine. Ethanolamine is a breakdown product of the membrane phospho lipid phosphatidylethanolamine (PE) and is prevalent in the gastrointestinal tract. Ethanolamine can be used as a source of nitrogen, and sometimes carbon, by bacteria capable of catabolizing this compound. However, up until now, it was only thought that pathogenic bacteria, such as enterohemorrhagic *Escherichia coli* O157: H7 (EHEC), were capable of utilizing ethanolamine. Such utilization in non-pathogenic bacteria can for example be detected in colonies on an agar plate by identifying a resulting acetaldehyde from the ethanolamine.

These findings will also make it possible to identify and select further lactic acid bacteria based on determining the presence of ethanolamine-utilizing properties of said bacteria. Accordingly, methods of selecting ethanolamine-utilizing lactic acid bacteria, methods of producing ethanolamine-utilizing lactic acid bacteria induced with ethanolamine as well as other uses, compositions and methods involving said novel strains and bacteria are also a result of these findings and therefore provided herein. These aspects are further described below.

Selection Method

Accordingly, in more detail, there is provided herein a method of selecting a lactic acid bacterial strain capable of utilizing ethanolamine, said method comprising the steps of:
  i) providing bacteria of a lactic acid bacterial strain in a culture medium and growing a culture of said bacteria,
  ii) determining if said bacteria are capable of utilizing ethanolamine; and
  iii) selecting said lactic acid bacterial strain if said bacteria are capable of utilizing ethanolamine, wherein said culture medium comprises an amount or concentration of ethanolamine and/or an amount or concentration of ethanolamine is added to the culture of step i) at a point in time before step ii).

Culture media contains nutrients and other ingredients to support the growth of bacterial cells, and are well known to the skilled person. Examples of culture media in the present context comprise e.g. agar (agar plates), but also liquid culture media are envisaged. A culture may also be referred to as the bacterial culture, and/or the media or medium as bacterial culture media/medium.

The culturing of said lactic acid bacteria in media comprising ethanolamine may be performed under anaerobic conditions, and at a temperature of about 35° C. to about 45° C., such as at about 37° C. Generally, the bacteria are allowed to grow for about 14 to about 72 hours, such as for about 20 to about 60 hours, about 14 to about 16 hours or for about 48 hours. Other, similar conditions are also envisaged, e.g. microaerobic conditions with less oxygen than in air (e.g. about 5% oxygen).

Ethanolamine may be added directly to the culture medium together with the lactic acid bacteria, such as when an agar plate is used in the method for determining if a lactic acid bacterial strain is capable of utilizing ethanolamine, but it may also be subsequently added, such as added at a later point in time, to an existing culture after the culture has been incubated for some time. Such a later point in time may e.g. be when the culture has reached a certain concentration or density, such as about 0.3-2 units measured as an optical density at 600 nm ($OD_{600}$).

The reference to an "amount or concentration" of e.g. ethanolamine herein is e.g. used to illustrate that the method may be performed in small or large scale, and also that suitable amounts and concentrations of ethanolamine may be used and envisaged in the methods of the present disclosure. Usually, ethanolamine will be described as being added in a certain concentration to the culture medium containing the lactic acid bacterial strain wherein the concentration is then the total concentration of ethanolamine in said medium when the ethanolamine has been added thereto, but of course this also means that an amount of ethanolamine is added to said culture medium to result in said concentration. The skilled person will know which amount or concentration of ethanolamine will be needed to induce and/or activate the bacterial culture.

The method may further comprise adding to the culture of step i) a further amount or concentration of ethanolamine at a second point in time, after a first amount of ethanolamine has been added, and growing said culture before performing steps ii) and iii) of said method. A further amount or concentration of ethanolamine, as described previously herein, may be added to the culture of lactic acid bacteria to further promote the induction of the utilization of ethanolamine by said bacteria and/or to further facilitate the production of acetaldehyde by said bacteria. If an agar media has been used, the bacteria have generally already been incubated in the presence of ethanolamine for a certain period of time. If so, any second amount or concentration of ethanolamine may be added as an overlay onto said agar plate containing the bacteria.

Illustrations of the method are presented in the experimental section.

A selection method provided herein may also include a further step, which step may be performed before the lactic acid bacteria have been exposed to ethanolamine. This is a step which comprises determining a certain genetic profile of said lactic acid bacteria, indicating if said bacteria are prone to utilize ethanolamine as a substrate. More specifically, such a method includes a further step which precedes step i) or is performed in association with step i) of the selection method and which comprises performing an initial screening of said lactic acid bacteria for the presence of one or more gene(s) encoding bacterial homologues of one or more of the genes encoding any of the proteins selected from the group consisting of: ethanolamine ammonia lyase large subunit EutB, microcompartment structural protein EutL and ethanolamine utilization protein EutH in said lactic acid bacteria.

"The genes are known and publicly available and can be found e.g. at NCBI GenBank®; according to the following information:
  1. Ethan olamine ammonia lyase large subunit EutB Example: Genbank accession number EOJ56712;
  2. Microcompartment structural protein EutL Example: Genbank accession number EOJ56710;
  3. Ethanolamine utilization protein EutH, ethanolamine transporter Example: Genbank accession number EOJ56702."

Optionally, the presence of a bacterial homologue of a gene encoding NADPH-dependent FMN reductase belonging to the pfam03358 protein family and/or a gene encoding Protein-tyrosine-phosphatase belonging to the pfam13350 protein family may also be determined in said method, sometimes referred to herein as a second or further genetic screening. Said genes may be present in the same gene cluster or operon as the above mentioned genes screened in the initial screening. Preferably said genes are present in the same gene cluster and sometimes even in the same operon as the genes of the initial screening.

By performing a second or further genetic screening described herein a method of selecting a lactic acid bacterial strain capable of utilizing ethanolamine comprising determining a genetic profile may be even further improved as these genes or all genes together are envisaged as particularly beneficial in the context of ethanolamine-utilization.

The NADPH-dependent FMN reductase belonging to the pfam 03358 protein may be exemplified by Genbank accession number WP_075913928, but is not limited thereto. The Protein-tyrosine-phosphatase belonging to the pfam13350 protein family may exemplified by Genbank accession number WP_054277074, but is not limited thereto.

As previously mentioned herein, the above mentioned genes, of said first or initial and said second or further screening may be present in the same gene cluster or even present in the same operon. In some aspects the genes above are present in the same gene cluster or same operon.

The presence of the one or more of the above mentioned genes in the genome of said lactic acid bacterial strain indicates that said strain is capable of using ethanolamine, and if so, a next step of determining or confirming if said strain is capable of utilizing ethanolamine, such as by determining the production of acetaldehyde may thereafter be performed.

The screening for the presence of said one or more gene(s) may be performed by generally known methods for analyzing genetic information e.g. by full or partial genome sequencing, polymerase chain reaction (PCR), microarrays or the like. These are all techniques that are well known to the skilled person and are easily retrievable.

The selection method may further comprise a step wherein step ii) comprises determining if said lactic acid bacteria are capable of producing acetaldehyde when utilizing ethanolamine, by measuring an amount or concentration of acetaldehyde in a culture sample from said bacterial culture. An example of how to determine if a lactic acid bacterial strain is capable of utilizing ethanolamine is found in example 1 of the experimental section (the results are shown in FIG. 1). Therein, the utilization was seen as a production of acetaldehyde from ethanolamine, visualized as red zones (marked with an arrow and also seen as to comprise a bold line) on an agar plate. See FIG. 1. The difference in the results between the ethanolamine-utilizing bacteria and bacteria not utilizing ethanolamine are clear, and are easy to determine for the skilled person. As a control reference, a lactic acid bacterial strain not capable of utilizing ethanolamine may be used, such as a strain identified as not possessing the genetic profile mentioned herein.

Accordingly, it is possible herein to determine if a lactic acid bacterial strain is capable of utilizing ethanolamine by analyzing the expansion or spread, but also measuring the width of the enlarged (red) zone surrounding the bold line comprising the bacterial streak as illustrated in FIG. 1. As previously mentioned herein, in some aspects, a lactic acid bacterial strain is determined to be ethanolamine-utilizing if a distinct red area or zone is observed on and/or around the bacterial streak demonstrating the presence of acetaldehyde. Sometimes, more specifically, a "width" of the zone may be measured and may extend at least about 0.5 mm on each side of the bold line or the bacterial streak, demonstrating the presence of acetaldehyde. This is also further shown in Example 1 and exemplified in Table 1.

Herein, an amount or concentration of ethanolamine in or added to said culture medium of step i) may be about about 0.1 mM to about 50 mM, such as about 1 mM to about 50 mM, such as about 1 mM to about 30 mM, such as about 0.5 mM to about 15 mM. This may also be referred to as the first amount or concentration of ethanolamine. In addition, the further amount or concentration of ethanolamine added to said culture may be about 1 mM to about 1M, such as about 30 mM to about 1M, or about 10mM to about 100 mM. This may also be referred to as a second amount or concentration of ethanolamine. The addition of the first or second amount of ethanolamine may, but need not necessarily, serve different purposes in the machinery of the ethanolamine-utilizing lactic acid bacteria.

Herein, and in all contexts, lactic acid bacteria may be bacteria of the genus *Lactobacillus*. This is indeed applicable to all aspects, uses and methods disclosed herein. Said lactic acid bacteria may also be bacteria of the species *Lactobacillus reuteri*. This is also applicable generally herein.

In an aspect of the disclosure, there is provided lactic acid bacteria of a lactic acid bacterial strain selected by the selection method herein, said bacteria being capable of utilizing ethanolamine.

Production Method

There is also provided a production method involving lactic acid bacteria as defined herein. More specifically, there is provided a method of producing lactic acid bacteria induced to utilize ethanolamine, said method comprising the steps of:
 i) providing lactic acid bacteria capable of utilizing ethanolamine in a culture medium,
 ii) adding to the culture of step i) a first effective amount or concentration of ethanolamine at a first point in time and growing said culture,
 iii) optionally adding to the culture of step ii) a second effective amount or concentration of ethanolamine at a second point in time and growing said culture, and thereafter;
 iv) retrieving the lactic acid bacteria from said culture medium.

The lactic acid bacteria produced by said method may in addition also be reuterin-producing and also be competing with pathogenic bacteria for the substrate glycerol or 1,2-propanediol (1,2-PD), thereby limiting the availability of such substrate for the pathogens, in addition to being limiting for the substrate ethanolamine. As previously mentioned herein, it is also envisaged that different mechanisms and parts of the lactic acid bacterial machinery, including the capability to utilize ethanolamine, may interact and thereby provide an improved antimicrobial effect.

Also in relation to the method of producing a lactic acid bacteria induced to utilize ethanolamine, a first and optionally a second amount or concentration of ethanolamine may be added or provided to said culture. This may also be referred to as a first and a second addition of ethanolamine to the culture or culture medium. Again, an amount or concentration of ethanolamine in or added to said culture medium of step i) may be about 1 to about 30 mM, or as exemplified elsewhere herein. This may also be referred to as the first amount or concentration of ethanolamine. Also, the further amount or concentration of ethanolamine added to said culture may be about 30 mM to about 1M, or as exemplified elsewhere herein. This may also be referred to as a second amount or concentration of ethanolamine. The addition of the first or second amount of ethanolamine may, but not necessarily, serve different purposes in the machinery of the ethanolamine-utilizing lactic acid bacteria.

As previously mentioned in relation to the selection method, the lactic acid bacteria used may be bacteria of the genus *Lactobacillus*. Further as previously mentioned, said lactic acid bacteria may be bacteria of the species *Lactobacillus reuteri*. This is equally applicable to all aspects herein.

The lactic acid bacteria produced by a method disclosed herein may subsequently be manufactured into a form suitable for storage, and subsequently into a product suitable for administration to human or animal subjects. The products should be substantially free from moisture to achieve satisfying storage stability (such as by adding an anti-moisture agent to said composition). The cultures of the lactic acid bacteria may be preserved in a frozen or lyophilized/freeze-dried form.

Of course, lactic acid bacteria used in any composition herein are viable bacteria, even if in a dried or lyophilized/freeze-dried form, or the like.

Accordingly, there is also provided herein a lactic acid bacteria produced by a method disclosed herein, as well as any composition comprising said lactic acid bacteria. Such a composition may be lyophilized/freeze-dried and may optionally contain further additives or ingredients, such as one or more cryoprotectants, lyoprotectant and/or anti-moisture agents.

Genetic Profiling

As previously mentioned herein there is in another aspect, but in relation to the selection method previously provided herein, provided a method of selecting a lactic acid bacterial strain capable of utilizing ethanolamine comprising determining a genetic profile of said lactic acid bacteria, said method comprising the steps of:
 i) providing bacteria of a lactic acid bacterial strain to be screened;
 ii) performing an initial screening of said lactic acid bacterial strain, to determine the presence of one or more of the bacterial homologues of the genes encoding the following proteins;
  a) Ethanolamine ammonia lyase large subunit EutB;
  b) Microcompartment structural protein EutL; and/or
  c) Ethanolamine utilization protein EutH; in said lactic acid bacterial strain
 iii) if one or more of said genes are present in said lactic acid bacterial strain, determining if said bacteria are capable of utilizing ethanolamine; and
 iv) selecting said lactic acid bacterial strain if said bacteria are capable of utilizing ethanolamine.

Optionally, a second or further screening, i.e. genetic screening, of said lactic acid bacterial strain may be performed, as a part of step ii), before or after step ii) and before step iii), or the like, of the above mentioned method, to determine the presence of one or more of the bacterial homologues of the genes encoding the following proteins: NADPH-dependent FMN reductase belonging to the pfam03358 protein family and/or Protein-tyrosine-phosphatase belonging to the pfam13350 protein family. Said genes may be present in the same gene cluster as the above mentioned genes screened in the initial screening, or even in the same operon. Preferably, said genes are present in the same gene cluster or even in the same operon. By performing a second genetic screening described herein a method of selecting a lactic acid bacterial strain capable of utilizing ethanolamine comprising determining a genetic profile may be further improved as these genes or all genes together are envisaged as beneficial in the context of ethanolamine-utilization.

The genes and the criteria for performing said method is as described previously herein in the context of a selection and/or production method.

Uses of Lactic Acid Bacteria Selected by, or Produced by a Method Herein, as well as Compositions Comprising Ethanolamine-Utilizing Lactic Acid Bacteria In yet another aspect there is provided lactic acid bacteria selected by, or produced by methods herein for use in inhibiting the growth of pathogenic bacteria in the gastrointestinal tract of an individual. Equally, there is provided the use of lactic acid bacteria selected by, or produced by methods herein for inhibiting growth of pathogenic bacteria. The suggested mechanism behind this feature of the selected or produced lactic acid bacteria has been previously described herein, and is due to the pathogenic bacteria and the lactic acid bacteria competing for the same substrate. By inhibiting the growth of these pathogens, any harmful effect to be caused by, or already caused by, the pathogen may indirectly be prevented or at least mitigated by the provision of the lactic acid bacteria to an individual in need thereof.

Hence, thereby, there is also provided herein such lactic acid bacteria, for use as a medicament. Furthermore, such lactic acid bacteria are provided for use in the treatment of a condition or disorder caused by or related to an ethanolamine-utilizing pathogen. As mentioned, such an effect may be mediated through the inhibiting effect of said lactic acid bacteria on the pathogenesis of the invading pathogenic bacteria. As shown herein, in example 3 and in FIG. 3, ethanolamine-utilizing lactic acid bacteria were capable of successfully inhibiting the growth of a pathogen, *C. difficile*.

Herein, said ethanolamine-using pathogen may be selected from the group consisting of *Clostridium difficile, Escherichia coli*, Enterohemorrhagic *Escherichia coli, Salmonella enterica* (e.g. *Salmonella enterica serovar typhimurium*), *Shigella sonnei, Shigella dysenteriae, Klebsiella pneumonia, Citrobacter koseri, Pseudomonas aeruginosa, Clostridium perfringens, Clostridium difficile, Clostridium tetani, Listeria monocytogenes, Fusobacterium nucleatum Enterococcus faecalis, Acinetobacter baumannii, Burkholderia mallei,* and *Burkholderia cepacia*. However, other ethanolamine-utilizing pathogens may also be envisaged.

Examples of conditions that have been associated with ethanolamine-utilizing pathogenic bacteria are e.g. dysbiosis (microbial imbalance or maladaptation on or inside the body), listeriosis, salmonellosis, bacterial infections leading to Inflammatory Bowel Disorders, infections with pathogenic pseudomonades (infected wounds), and tourist diarrhea.

There is also provided a composition comprising ethanolamine-utilizing lactic acid bacteria induced by ethanolamine during growing of a cell culture comprising said lactic acid bacteria. As previously described herein, a composition described herein may comprise lactic acid bacteria of the genus *Lactobacillus*. Said *Lactobacillus* may also be bacteria of the species *Lactobacillus reuteri*. The compositions herein may be for use in the treatment of a condition or disorder caused by or related to an ethanolamine-utilizing pathogen. The compositions herein may also be for use in inhibiting the growth of one or more pathogenic bacteria in the gastrointestinal tract of an individual. Equally, they may be used for the treatment of a condition or disorder caused by or related to an ethanolamine-utilizing pathogen and in inhibiting the growth of one or more pathogenic bacteria in the gastrointestinal tract of an individual.

Naturally, there is provided herein said ethanolamine-utilizing lactic acid bacteria or lactic acid bacterial strains for use a probiotic. There is also provided a probiotic composition comprising said lactic acid bacteria or lactic acid bacterial strains in all aspects presented herein.

Novel Lactic Acid Bacterial Strains

There is also provided the following novel lactic acid bacterial strains:

a biologically pure culture of *Lactobacillus reuteri* DSM 27131 and;

a biologically pure culture of *Lactobacillus reuteri* DSM 32465.

In an aspect thereof, there is provided a frozen or lyophilized composition(s) comprising a biologically pure culture of any one of strains *Lactobacillus reuteri* DSM 27131 and *Lactobacillus reuteri* DSM 32465.

There is also provided herein novel frozen or lyophilized products of *Lactobacillus reuteri* containing at least a:

a biologically pure culture of *Lactobacillus reuteri* DSM 27131; or a biologically pure culture of *Lactobacillus reuteri* DSM 32465.

There is also provided herein, the following novel frozen products of *Lactobacillus reuteri* containing at least a cryoprotectant, such as glycerol, and:

A biologically pure culture of *Lactobacillus reuteri* DSM 27131; or a biologically pure culture of *Lactobacillus reuteri* DSM 32465.

There is also provided herein, the following novel lyophilized products of *Lactobacillus reuteri* containing at least a lyoprotectant, such as a disaccharide, and:

A biologically pure culture of *Lactobacillus reuteri* DSM 27131; or a biologically pure culture of *Lactobacillus reuteri* DSM 32465.

Herein, the terms products and compositions may be used interchangeably in relation to said lactic acid bacteria.

As previously mentioned herein, there is provided the novel *Lactobacillus reuteri* strains described herein, or the compositions or products comprising or containing said strains for use in the treatment of a condition or disorder caused by or related to an ethanolamine-utilizing pathogen and/or for use in inhibiting the growth of one or more pathogenic bacteria in the gastrointestinal tract of an individual, as previously described herein. The ethanolamine-utilizing pathogens are exemplified elsewhere herein and equally applicable in the present context.

There is also provided a method for the treatment of a condition or disorder caused by or related to an ethanolamine-utilizing pathogen in an individual, said method comprising administering to said individual an effective amount of a lactic acid bacteria, a novel lactic acid bacterial strain or a composition, or a products as described elsewhere herein to said individual. There is also provided a method for the treatment of an individual suffering from an infection with pathogenic ethanolamine-utilizing bacteria by administering ethanolamine-utilizing lactic acid bacteria as defined herein, to inhibit the growth of said pathogenic bacteria. A pharmaceutically effective amount of said lactic acid bacteria is administered to said individual, to be determined by the skilled practitioner.

There is also provided a method for the improvement of a *Lactobacillus* strain, such as a *Lactobacillus reuteri* to bile by dominant selection—Bile tolerance, as further described in the examples below (example 2). Accordingly, in example 2 it is shown that a *Lactobacillus reuteri* strain DSM 32465, modified from the wildtype strain, *Lactobacillus reuteri* DSM 27131, is more resistant to bile than the wildtype strain. This presents a further advantage of *L. reuteri* strain DSM 32465 for use as a probiotic for certain conditions, uses and indications.

The present invention will now be illustrated by the following experimental section, but it is not intended to be limited thereto.

EXPERIMENTAL SECTION

Example 1

Selection of a Bacterial Strain that can Utilize Ethanolamine
Bacterial Strains
Different strains of *Lactobacillus reuteri* were tested; *L. reuteri* DSM 27131, *L. reuteri* DSM 17938 and *L. reuteri* DSM 32465. All strains were obtained from BioGaia AB.
Method
The bacteria were grown for 48 hours on MRS agar plates (with 10 mM ethanolamine) in anaerobic atmosphere at 37° C. The plates were then overlaid with 500 mM ethanolamine agar (1% agar) and incubated at 37° C. for 1 hour. Acetaldehyde was detected by the addition of 5 ml 2,4-dinitrophenylhydrazine (0.1% in 2 M HCl). After 3 min incubation, the solution was poured off and 5 ml 5 M KOH was added. Red zones around the bacterial streaks demonstrated the presence of acetaldehyde.
Results
All strains of *L. reuteri* were tested for their possible utilization of ethanolamine which would be seen as the production of acetaldehyde. *L. reuteri* DSM 17938 was negative but *L. reuteri* DSM 27131 and *L. reuteri* DSM 32465 were positive in this assay, see FIG. 1. Accordingly, enlarged (red) zones were seen around *L. reuteri* DSM 27131 and *L. reuteri* DSM 32465. No enlarged (red) zone was seen around *L. reuteri* DSM 17938. The approximate widths of the acetaldehyde-containing zones in FIG. 1 are illustrated in Table 1 below.

TABLE 1

Widths of red zones surrounding bacterial streaks in
FIG. 1, B (DSM 27131) and C (DSM 32465), respectively

| Strain | Bacterial streak width (mm) | Width with zones (mm) | Only zone, size (mm) | Zone size, on each side (mm) |
| --- | --- | --- | --- | --- |
| DSM 27131 | 10 | 16 | 6 | 3 |
| DSM 32465 | 14 | 17 | 3 | 1.5 |

| | Normalized values | | | |
| --- | --- | --- | --- | --- |
| Strain | Bacterial streak width (mm) | Width with zones (mm) | Only zone, size (mm) | Zone size, on each side (mm) |
| DSM 27131 | 4 | 6.40 | 2.40 | 1.20 |
| DSM 32465 | 4 | 4.86 | 0.86 | 0.43 |

Selection Step
*Lactobacillus reuteri* DSM 27131 and *Lactobacillus reuteri* DSM 32465 were selected.

Example 2

Improvement of *Lactobacillus Reuteri* by Dominant Selection—Bile Tolerance
Bacterial Strains
*Lactobacillus reuteri* strain DSM 27131 was used.
Method
The bacteria were grown overnight (ON) in MRS broth at 37° C. The tubes were then centrifuged at 3000× g for 10 minutes and the supernatant was discarded. The pellet was re-suspended in equal amounts of MRS with added porcine bile (0.5% w/v). Aliquots of 200 μl were prepared, two tubes were taken directly for viability assay (starting value). Serial tenfold dilutions were made for these tubes were made and plated on MRS agar plates, using a drop-plate method. Briefly, 10 μl of each dilution was dropped onto a MRS plates divided into six zones, left to dry before being incubated ON in anaerobic atmosphere at 37° C. The rest of the aliquots were incubated at 37° C., two tubes were taken every 30 min for viability assay for up to four hours.

Figure 2:
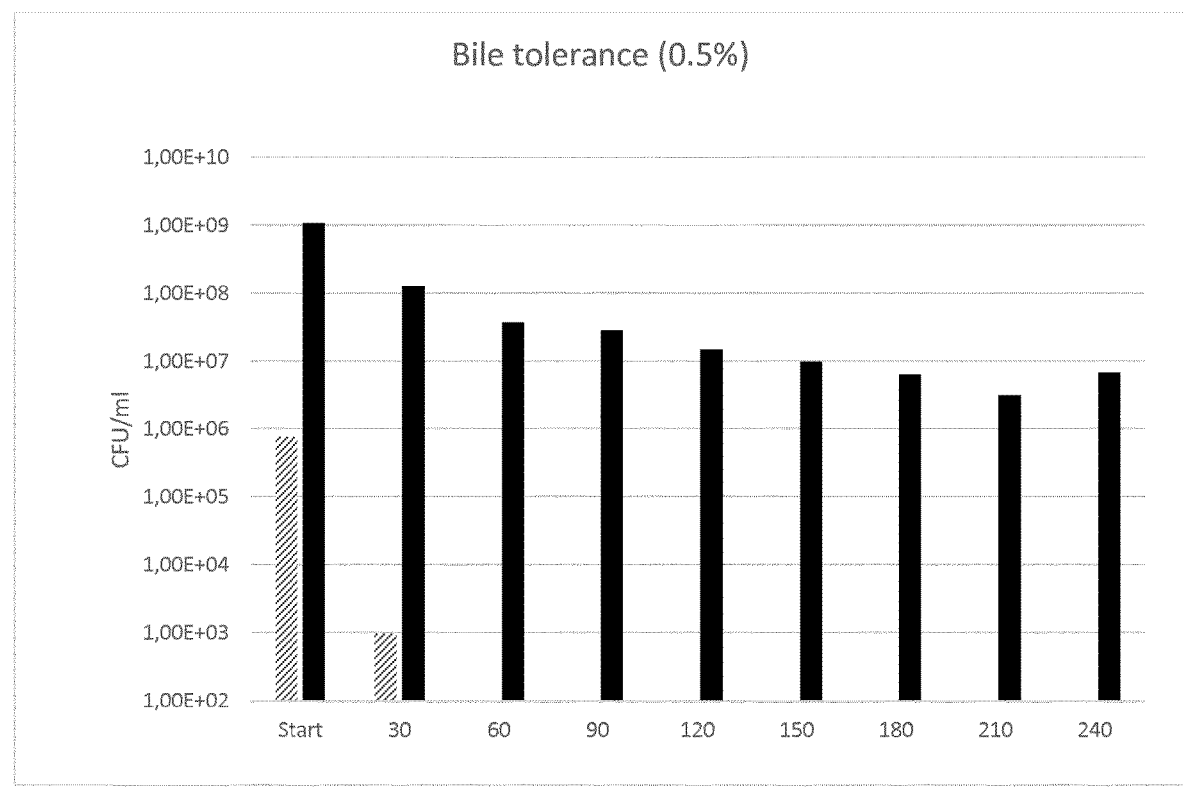
FIG. 2 shows a bile tolerance assay and the decline of viability of the wild type strain of *L. reuteri* DSM 27131 (in grey/striped bars) and improved strain *L. reuteri* DSM 32465 (in black bars).

After ON incubation, the bacterial counts were determined to establish the viability of the bacteria. From appropriate time points, depending on the viability, colonies of different sizes were collected and saved as new varieties of the same strain of *L. reuteri*.
Selection Step
The new variety *Lactobacillus reuteri* DSM 32465 was selected.
Results
Initial tests with *L. reuteri* DSM 27131 showed poor tolerance to porcine bile at concentrations of 1 and 5%. An additional experiment was made with 0.5% of porcine bile with the same results as before, however from the first two time points, colonies were picked and saved as new varieties. *Lactobacillus reuteri* DSM 32465 were tested in the same way as *L. reuteri* DSM 27131, with 0.5% bile and showed a significant improvement in bile tolerance (FIG. 2). The low starting value of *L. reuteri* DSM 27131 shows how sensitive the wild type is to porcine bile with a decline from approximately $5 \cdot 10^8$ CFU/ml to below $10^6$ in a matter of a few minutes.

Example 3

Figure 3:
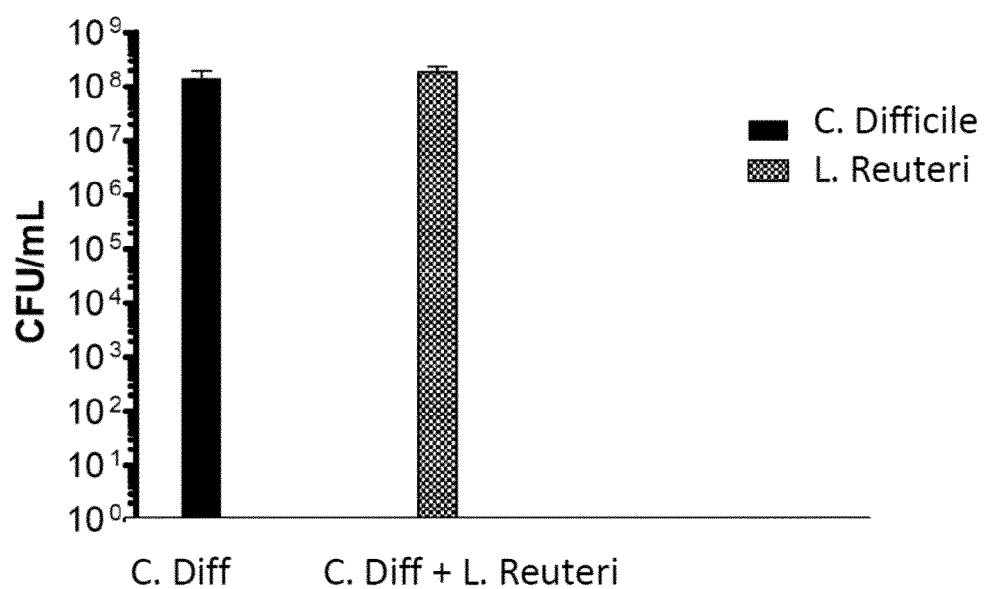
FIG. 3. Ex vivo analysis confirms enhanced inhibition of *C. difficile* by *L. reuteri* DSM 27131 preincubated with 10 mM ethanolamine. Ex vivo outgrowth of *C. difficile* CD2015 was measured in fecal contents from germ-free mice. Results for viable colony forming units of *C. difficile* and *C. difficile* together with *L. reuteri* DSM 27131 after incubation for 24 h. Data represent the mean±S.D.

Results
Ex vivo experiments show that ethanolamine-utilizing strain *L. reuteri* strain DSM 27131 completely inhibits the growth of *C. difficile* while *L. reuteri* DSM 17938 (data not shown) did not inhibit the growth of *C. difficile* during the same experimental conditions (FIG. 3).
Materials & Methods
Bacterial Strains and Culture Conditions.
Routine culturing of *Lactobacillus reuteri* strains 17938 and DSM 27131 in deMan, Rogosa, Sharpe medium (MRS; Difco, Franklin Lakes, N.Y.) and *C. difficile* CD2015 in Brain Heart Infusion medium with 2% D-glucose (w/v) (BHI; BD Biosciences, Franklin Lakes, N.J.) was carried out at 37° C. in an anaerobic chamber (Anaerobe Systems, AS-580, Morgan Hill, Calif.) supplied with a mixture of 10% $CO_2$, 5% $H_2$, and 85% $N_2$ for 16-18 h.
Ex Vivo Outgrowth Studies in GI Fecal Content.
The susceptibility of *C. difficile* to *L. reuteri* 17938 or *L. reuteri* DSM 27131 in germ-free mouse fecal content was determined as follows. Fecal pellets were collected from germ-free 7-10 wk old C57BL/6 mice, resuspended 1:2 in PBS and aliquoted to 200 μL samples. Each aliquot was inoculated with *C. difficile* CD2015 ($10^4$/mL) and then incubated with PBS containing 3 mM glycerol and treated with *L. reuteri* 17938 ($10^7$/ml) or *L. reuteri* DSM 27131 ($10^7$/ml, preincubated overnight with 10 mM ethanolamine). Suspensions were incubated anaerobically at 37° C. for 24 h. Samples were taken at 0 and 24 h and *C. difficile* and *L. reuteri* bacteria were quantified by overnight culture on pre-reduced selective cycloserine-cefoxitin-fructose agar with sodium taurocholate (TCCFA) or MRS media respectively. Plates were incubated anaerobically for 48 h at 37° C. and colony forming units counted.

Example 4

Partial Sequencing of Bacterial Homologues of the Genes of a Genetic Screening Method Presented Herein A draft genome sequence was obtained by using methods known in the art on bacterial strain *L. reuteri* DSM 27131. The result of this analysis demonstrate that the following genes encoding proteins involved in ethanolamine utilization were found in bacterial strain *L. reuteri* DSM 27131:
 1. Ethanolamine ammonia lyase large subunit EutB
 2. Microcompartment structural protein EutL
 3. Ethanolamine utilization protein EutH
 4. NADPH-dependent FMN reductase belonging to the pfam03358 protein family
 5. Protein-tyrosine-phosphatase belonging to the pfam13350 protein family All genes above were present in the same gene cluster, and also likely in the same operon.

The invention claimed is:

1. A composition comprising frozen and/or lyophilized probiotic *Lactobacillus reuteri* DSM 27131 and one or more of a cryoprotectant and/or a lyoprotectant.

2. A biologically pure culture of *Lactobacillus reuteri* DSM 32465.

3. The biologically pure culture of claim 2, wherein the *Lactobacillus reuteri* DSM 32465 is frozen and/or lyophilized.

4. A composition comprising probiotic *Lactobacillus reuteri* DSM 32465 and one or more of a cryoprotectant and/or a lyoprotectant.

5. A method for treating or reducing the risk of developing a condition or disorder caused by or related to an ethanolamine-utilizing pathogen in a subject in need thereof, said method comprising administering an effective amount of a composition comprising *Lactobacillus reuteri* DSM 32465 and/or *Lactobacillus reuteri* DSM 27131 to the subject.

6. The method of claim 5, wherein said ethanolamine-using pathogen is selected from the group consisting of *Clostridium difficile, Escherichia coli*, Enterohemorrhagic *Escherichia coli, Salmonella typhimurium, Salmonella enterica serovar Typhimurium, Shigella sonnei, Shigella dysenteriae, Klebsiella pneumoniae, Citrobacter koseri, Pseudomonas aeruginosa, Clostridium perfringens, Clostridium difficile, Clostridium tetani, Listeria monocytogenes, Fusobacterium nucleatum, Enterococcus faecalis, Acinetobacter baumannii, Burkholderia mallei*, and *Burkholderia cepacia*.

7. The method of claim 5, wherein the condition or disorder caused by or related to an ethanolamine-utilizing pathogen is dysbiosis (microbial imbalance or maladaptation on or inside the body), listeriosis, salmonellosis, bacterial infections leading to Inflammatory Bowel Disorders, infections with pathogenic pseudomonades (infected wounds), and/or tourist diarrhea.

* * * * *